United States Patent [19]

Urano et al.

[11] Patent Number: 5,498,748

[45] Date of Patent: Mar. 12, 1996

[54] ANTHRACENE DERIVATIVES

[75] Inventors: Fumiyoshi Urano; Keiji Oono; Hiroshi Matsuda, all of Kawagoe, Japan

[73] Assignee: Wako Pure Chemical Industries, Ltd., Osaka, Japan

[21] Appl. No.: 272,753

[22] Filed: Jul. 11, 1994

[30] Foreign Application Priority Data

Jul. 20, 1993 [JP] Japan .................................. 5-200364

[51] Int. Cl.$^6$ .................................................. C07C 69/88
[52] U.S. Cl. .................................................... 560/67
[58] Field of Search ................................................ 560/67

[56] References Cited

U.S. PATENT DOCUMENTS 4,843,097  6/1989  Shroot et al. .

FOREIGN PATENT DOCUMENTS

| 0233056 | 8/1987 | European Pat. Off. . |
| 2257442 | 11/1972 | Germany . |
| 3642247 | 6/1987 | Germany . |
| 59-93448 | 5/1984 | Japan . |
| 59-135748 | 8/1984 | Japan . |
| 4-298505 | 10/1992 | Japan . |
| 5-47656 | 2/1993 | Japan . |

OTHER PUBLICATIONS

J. Chem. Soc. (C), The Formation of Chromanone-type Systems via the Acylation of Derivatives of 2,6-Dihydroxyanthracene, by D. W. Cameron and P. E. Schütz, Univ. Chemical Laboratory, Cambridge, 1967.

*Primary Examiner*—Paul J. Killos
*Attorney, Agent, or Firm*—Armstrong, Westerman, Hattori, McLeland & Naughton

[57] ABSTRACT

An anthracene derivative having at least two groups of the formula:

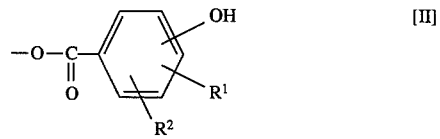

wherein $R^1$ and $R^2$ are independently hydrogen, alkyl, alkoxy, etc., is particular effective for forming an antireflection coating for preventing multiple reflection of exposing light from a highly reflective substrate, etc.

5 Claims, 2 Drawing Sheets

FIG. I
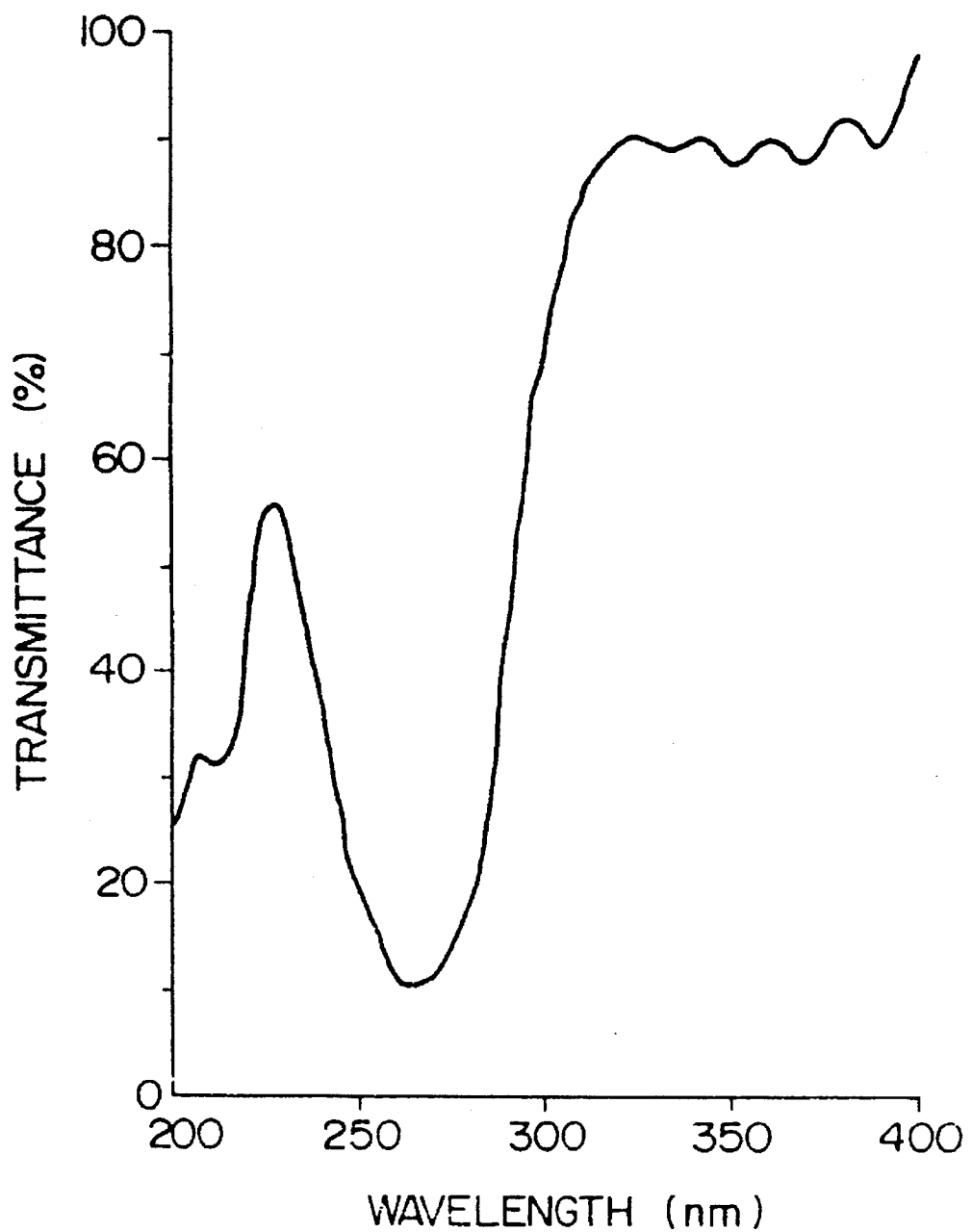

ANTHRACENE DERIVATIVES

BACKGROUND OF THE INVENTION

This invention relates to an anthracene derivative usable as a material for semiconductors, an intermediate for medicines, an intermediate for dyes and a functional material for optical recording materials, etc., and particularly useful as a material for producing an antireflection coating in the field of semiconductors.

Chemically amplified resist materials are now studied for applying to fine pattern formation using deep ultraviolet light (300 nm or less), such as KrF excimer laser beams (248.4 nm). But when these resist materials are used for highly reflective substrates such as aluminum wired substrates, there arise strong influences by in-layer multiple reflection caused by reflection of exposing light from semiconductor substrates due to high transmittivity of the resist materials for deep ultraviolet light, etc. When film thickness of resists is changed remarkably by level difference, etc. caused by the influences of in-layer multiple reflection, resist pattern dimension changes greatly, resulting in causing a problem of disconnection, and the like. In order to prevent the in-layer multiple reflection, the formation of an antireflection coating on a semiconductor substrate is now studying. But no suitable materials usable as antireflection coating for deep ultraviolet light such as KrF excimer laser beams are found yet.

SUMMARY OF THE INVENTION

It is an object of the present invention to provide an anthracene derivative usable as an intermediate for medicines, dyes, etc., a material for optical recording materials and semiconductors, particularly as a material for forming an antireflection coating on a surface of a semiconductor substrate in order to prevent influences of the in-layer multiple reflection at the time of resist pattern formation by lithograph using deep ultraviolet light such as KrF excimer laser beams and to satisfy the recent demand.

The present invention provides an anthracene derivative of the formula:

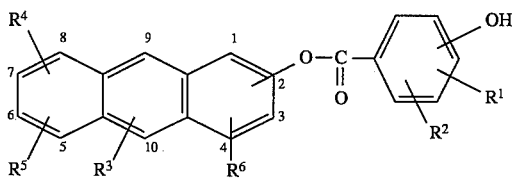

wherein $R^1$ and $R^2$ are independently a hydrogen atom, an alkyl group, an alkoxy group, a halogen atom or a hydroxyl group; $R^3$, $R^4$, $R^5$ and $R^6$ are independently a hydrogen atom, an alkyl group, an alkoxy group, a halogen atom, or a group of the formula:

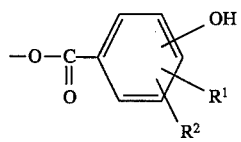

wherein $R^1$ and $R^2$ are as defined above, provided that at least one of $R^3$ through $R^6$ is the group of the formula [II], and the group of the formula [II] in number of 3 cannot be positioned at the 1, 8 and 9 positions of the anthracene ring at the same time.

BRIEF DESCRIPTION OF THE DRAWINGS

FIG. 1 shows a ultraviolet spectroscopic curve of the antireflection coating obtained in Reference Example 2.

DESCRIPTION OF THE PREFERRED EMBODIMENTS

Figure 2A:
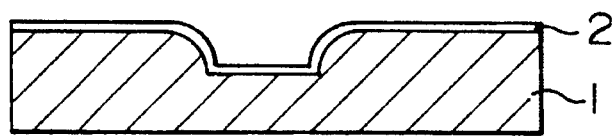
FIGS. 2A to 2E are cross-sectional views explaining the formation of a pattern using an antireflection coating material using the anthracene derivative of the present invention as an undercoating agent.

The anthracene derivative of the present invention is represented by the formula:

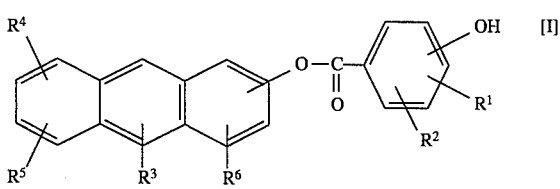

wherein $R^1$ and $R^2$ are independently a hydrogen atom, a lower alkyl group preferably having 1 to 6 carbon atoms, more preferably 1 to 4 carbon atoms, a lower alkoxy group preferably having 1 to 6 carbon atoms, more preferably 1 to 4 carbon atoms, a halogen atom such as chlorine, bromine and iodine, or a hydroxyl group; $R^3$, $R^4$, $R^5$ and $R^6$ are independently a hydrogen atom, a lower alkyl group preferably having 1 to 6 carbon atoms, more preferably 1 to 4 carbon atoms, a lower alkoxy group preferably having 1 to 6 carbon atoms, more preferably 1 to 4 carbon atoms, a halogen atom such as chlorine, bromine or iodine, or a group of the formula:

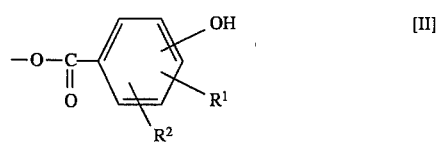

wherein $R^1$ and $R^2$ are as defined above, provided that at least one of $R^3$ to $R^6$ is the group of the formula [II], and the group of the formula [II] in number of 3 cannot be positioned at the 1, 8 and 9 positions of the anthracene ring at the same time.

The anthracene derivative of the formula [I] is particularly effective as a material for preparing an antireflection coating, which is used for preventing reflection of exposing light from a substrate at the time of resist pattern formation by lithography using deep ultraviolet light such as KrF excimer laser beams and is required to absorb deep ultraviolet light, to improve heat resistance of the antireflection coating and to have an ability not causing intermixing of the antireflection coating with a resist material coated thereon at the interface. In search of a compound that can meet these requirements, the present inventors noticed a series of compounds having in the molecule two or more phenolic hydroxyl groups which are capable of causing crosslinking reaction with a resin having one or more glycidyl groups on heating and also having in the molecule an anthracene skeleton showing strong absorption at around 220–300 nm. As a result, the present inventors have successfully found out the compounds represented by the formula [I] having electron attractive groups such as -OCO- group introduced into the p- or m-position with regard to the phenolic hydroxyl group for facilitating said thermal crosslinking reaction.

In the compounds of the formula [I], when the group of the formula [II] in number of 3 is positioned at the 1, 8 and 9 positions of the anthracene ring at the same time, the resulting compounds do not bring about crosslinking reaction with a compound (or resin) having one or more glycidyl groups, resulting in failing to form a desirable antireflection coating. Further, when one or more phenolic hydroxyl groups are positioned at para and/or meta positions with regard to the -O-CO- group in the formula [I], crosslinking reaction with a compound (or resin) having one or more glycidyl groups is remarkably increased to give a desirable antireflection coating.

The compounds represented by the formula [I] can be easily synthesized by, for example, the following method (a), (b) or (c).

(a) Method 1

In the case of a compound of the formula [I] wherein $R^3$ is a group of the formula [II]; $R^4$, $R^5$ and $R^6$ are each a hydrogen atom, an alkyl group, a halogen atom or a group of the formula [II], it can be easily synthesized according to the following reaction scheme 1:

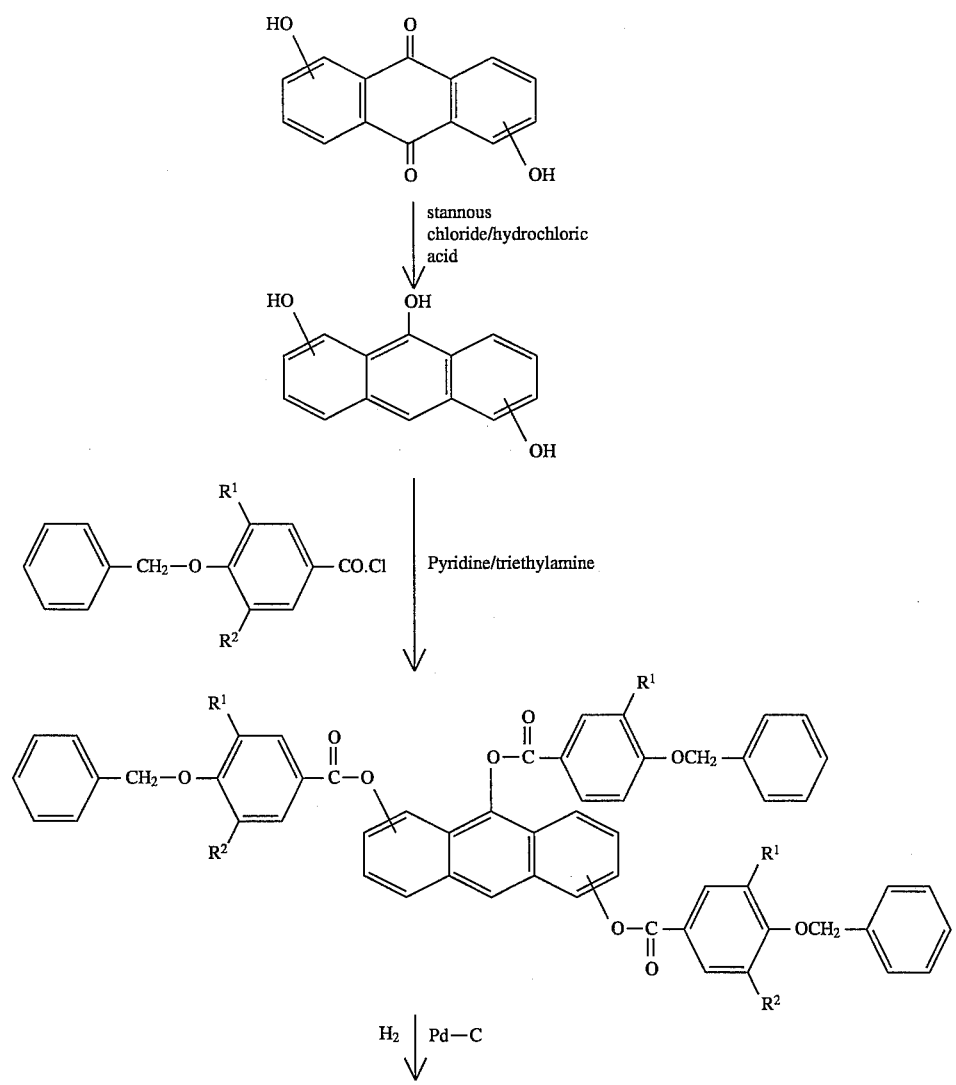

-continued
<Reaction scheme 1>

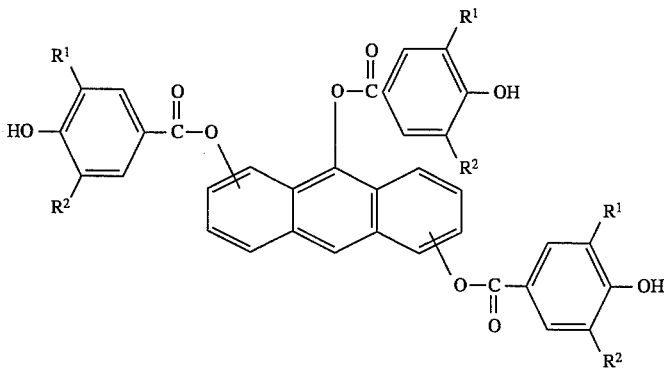

In the above reaction, first an anthraquinone derivative having at least one hydroxyl group is dissolved in 5–20 times as large as in volume of acetic acid or propionic acid, followed by addition of excess amounts of concentrated hydrochloric acid and stannous chloride to carry out a reducing reaction at 10° to 120° C. to form an anthracenetriol derivative.

This anthracenetriol derivative (1 mole) is reacted with 2 moles or more (3 moles in the reaction scheme 1) of p-benzyloxybenzoyl chloride in the presence of 2 moles or more (3 moles in the reaction scheme 1) of a base (e.g. triethylamine, piperidine, NaOH, KOH, NaH or the like) in 1–20 times as much volume of a suitable organic solvent (e.g., triethylamine, pyridine, methylene chloride, toluene, ethyl ether, tetrahydrofuran or the like) at 0°–150° C. for 30 minutes to 20 hours to give an objective compound wherein the hydroxyl group is protected (benzyl group in the case of the reaction scheme 1).

This compound is then subjected to hydrogenation reaction in 1–20 times as much volume of a suitable organic solvent (e.g., methanol, ethanol, propanol, isopropanol, tetrahydrofuran, methylene chloride, chloroform or the like) in the presence of a catalyst such as Raney nickel, palladium on carbon or the like under normal pressure to 50 kg/cm² (initial hydrogen pressure) at 0°–50° C. for 1–10 hours to give an objective compound of the formula [I].

(b) Method 2

In the case of a compound of the formula [I] wherein $R^3$ is a hydrogen atom; $R^4$ or $R^6$ is a group represented by the formula [II]; and $R^6$ or $R^4$ and $R^5$ are a hydrogen atom, an alkyl group or a halogen atom, it can be synthesized according to the following reaction scheme 2:

<Reaction scheme 2>

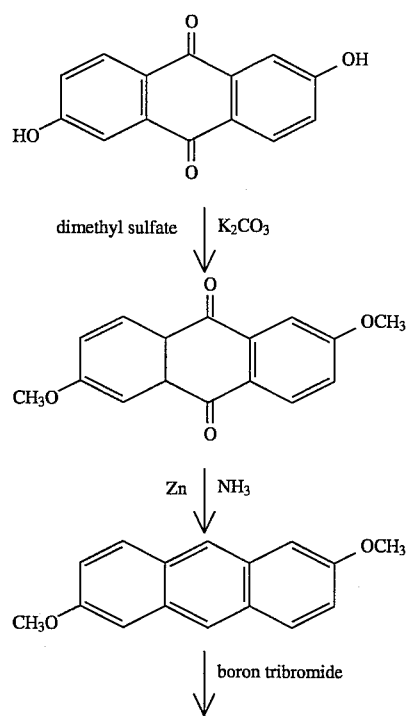

-continued
<Reaction scheme 2>

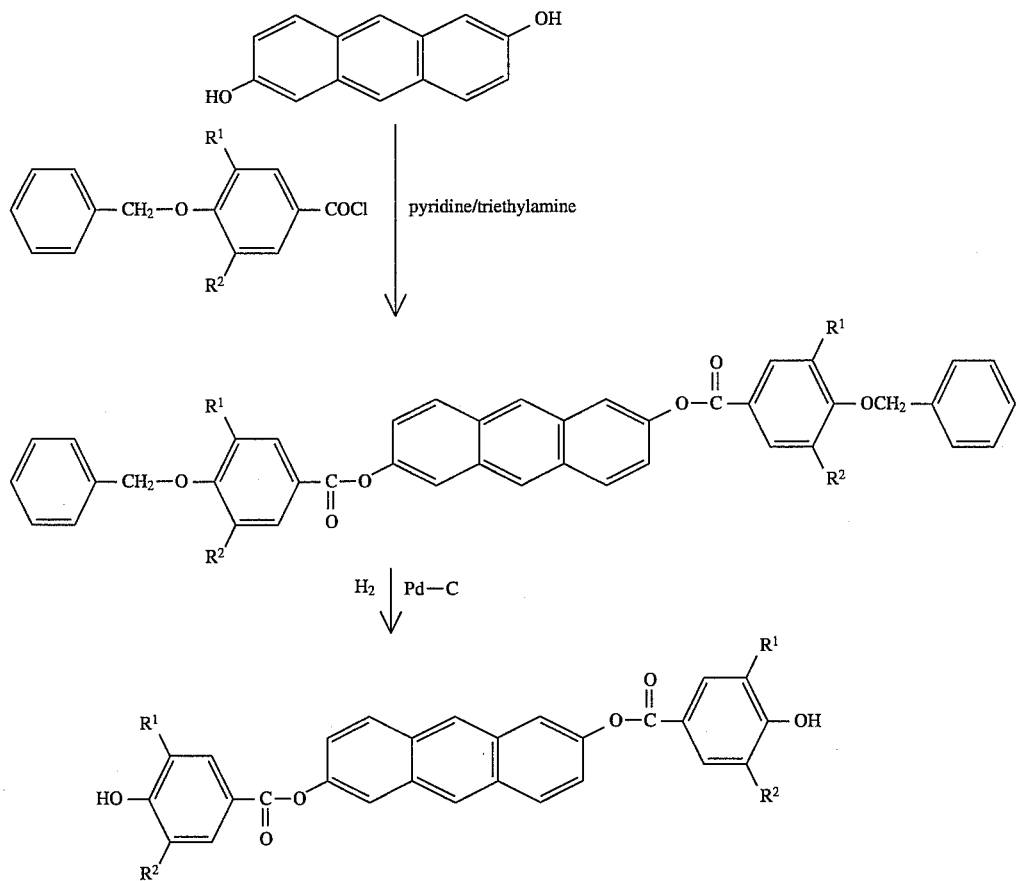

An anthraquinone derivative having 2 hydroxyl groups, for example, 2,6-dihydroxyanthraquinone, is reacted with an alkylating agent such as dimethyl sulfate, in the presence of a base such as anhydrous potassium carbonate, etc. to protect the hydroxyl groups, and then reduced with zinc/ammonia water to give, for example, 2,6-dimethoxyanthracene having the protected hydroxyl groups at the 2,6-positions. Then the protective groups of hydroxyl groups are eliminated by reaction with, for example, boron tribromide to form 2,6-dihydroxyanthracene. This is esterified with p-benzyloxybenzoyl chloride, etc. and subjected to hydrogenation reaction to eliminate the protective groups (benzyl group) in the same way as in the above-described method (a) to give a compound of the formula [I].

(c) Method 3

In the case of a compound of the formula [I] wherein $R^3$ is hydrogen atom; $R^4$ and $R^6$ are a group represented by the formula [II]; and $R^5$ is a hydrogen atom, an alkyl group, a halogen atom or a group represented by the formula [II], it can easily be synthesized according to the following reaction scheme 3:

<Reaction scheme 3>

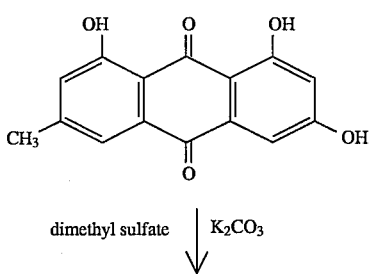

-continued
<Reaction scheme 3>

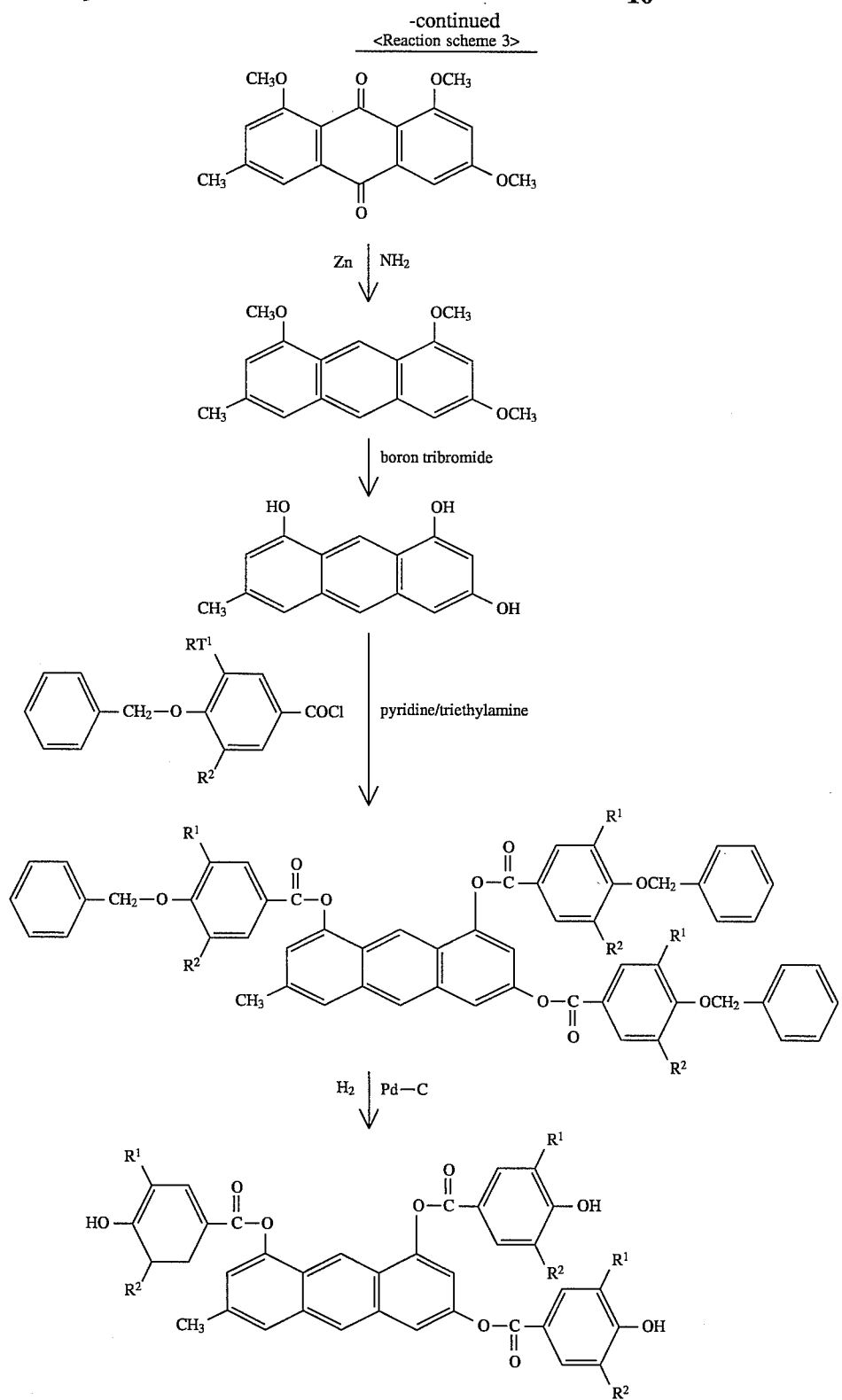

An anthraquinone derivative having 3 or more hydroxyl groups, for example, 6-methyl-1,3,8-trihydroxyanthraquinone, is reacted according to the above-described method (b) to effect alkyl etherification of the hydroxyl groups and then reduced with zinc/ammonia water to give, for example, 6-methyl-1,3,8-trimethoxyanthracene having the protected hydroxyl groups at the 1,3,8-positions. Then the protective groups of this hydroxyl groups are eliminated by reaction with, for example, boron tribromide to form 6-methyl-1,3,8-trihydroxyanthracene. This is esterified with p-benzyloxybenzoyl chloride, etc. and then the protective groups (benzyl groups) of the hydroxyl groups are eliminated by catalytic reduction or other means to give an objective compound of the formula [I].

The following are the examples of the compounds represented by the formula [I]:
2,6,9-tris(4-hydroxybenzoyloxy)anthracene,
2,6,9-tris(3,4-dihydroxybenzoyloxy)anthracene,
2,6,9-tris(3-hydroxybenzoyloxy)anthracene,
2,6,9-tris(4-hydroxy-3-methoxybenzoyloxy)anthracene,
2,6,9-tris(3-chloro-4-hydroxybenzoyloxy)anthracene,
2,6,9-tris(3-hydroxy-4-methylbenzoyloxy)anthracene,
1,2-10-tris(4-hydroxybenzoyloxy)anthracene,
1,2,10-tris(3-hydroxybenzoyloxy)anthracene,
1,2,10-tris(3,4-dihydroxybenzoyloxy)anthracene,
1,2,10-tris(4-hydroxy-3-methoxybenzoyloxy)anthracene,
1,2,10-tris(3-hydroxy-4-methylbenzoyloxy)anthracene,
1,2,10-tris(3-chloro-4-hydroxybenzoyloxy)anthracene,
1,5,9-tris(4-hydroxybenzoyloxy)anthracene,
1,5,9-tris(3-hydroxybenzoyloxy)anthracene,
1,5,9-tris(3,4-dihydroxybenzoyloxy)anthracene,
1,5,9-tris(4-hydroxy-3-methoxybenzoyloxy)anthracene,
1,5,9-tris(3-hydroxy-4-methylbenzoyloxy)anthracene,
1,5,9-tris(3-chloro-4-hydroxybenzoyloxy)anthracene,
1,4,9-tris(4-hydroxybenzoyloxy)anthracene,
1,5-bis(4-hydroxybenzoyloxy)anthracene,
1,5-bis(3-hydroxybenzoyloxy)anthracene,
1,5-bis(3,4-dihydroxybenzoyloxy)anthracene,
1,5-bis(4-hydroxy-3-methoxybenzoyloxy)anthracene,
1,5-bis(3-chloro-4-hydroxybenzoyloxy)anthracene,
1,5-bis(3-hydroxy-4-methylbenzoyloxy)anthracene,
2,6-bis(4-hydroxybenzoyloxy)anthracene,
2,6-bis(3-hydroxybenzoyloxy)anthracene,
2,6-bis(3,4-dihydroxybenzoyloxy)anthracene,
2,6-bis(4-hydroxy-3-methoxybenzoyloxy)anthracene,
2,6-bis(3-chloro-4-hydroxybenzoyloxy)anthracene,
2,6-bis(3-hydroxy-4-methylbenzoyloxy)anthracene,
1,2-bis(4-hydroxybenzoyloxy)anthracene,
1,2-bis(4-hydroxy-3-methoxybenzoyloxy)anthracene,
1,8-bis(4-hydroxybenzoyloxy)-3-methylanthracene,
6,7-dichloro-1,4-bis(4-dihydroxybenzoyloxy)anthracene,
6-methyl-1,3,8-tris(4-hydroxybenzoyloxy)anthracene,
1,4-bis(3,4-dihydroxybenzoyloxy)anthracene,
6-methyl-1,3,8,10-tetra(4-hydroxybenzoyloxy)anthracene,
1,10-bis(4-hydroxybenzoyloxy)-2-methoxyanthracene,
2,6-bis(4-hydroxybenzoyloxy)-9-methoxyanthracene,
2,3-dimethyl-1,4,9-tris(4-hydroxybenzoyloxy)anthracene,
1,4-bis(3,4-dihydroxybenzoyloxy)-2,3-dimethylanthracene,
1,2,5,8-tetra(4-hydroxybenzoyloxy)anthracene,
5,8-dichloro-1,4,9-tris(4-hydroxybenzoyloxy)anthracene,
etc.

The formation of an antireflection coating using the anthracene derivative of the formula [I] is explained below.

An anthracene derivative of the formula [I] and a resin having at least one glycidyl group (an epoxy group) in the molecule, for example, a homopolymer or copolymer of glycidyl methacrylate are dissolved in a suitable organic solvent such as propylene glycol monomethyl ether acetate, tetrahydrofurfuryl alcohol, diethylene glycol dimethyl ether, etc. The resulting mixture is spin coated on a semiconductor substrate and heat at 150° C. or higher. Then, a crosslinking reaction between the glycidyl groups of the resin and the anthracene derivative of the formula [I] takes place as shown in the following formula (4) to give an antireflection coating excellent in heat resistance. Both the anthracene derivative of the formula [I] which functions as a crosslinking agent, and the resin having one or more glycidyl(epoxy) groups in the molecule are soluble in acetone and a solvent for resist materials, but the antireflection coating obtained by the crosslinking reaction of the formula (4) is not soluble in the above-mentioned solvents.

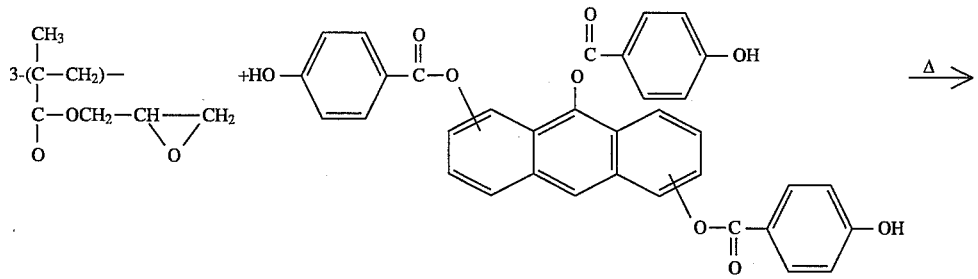

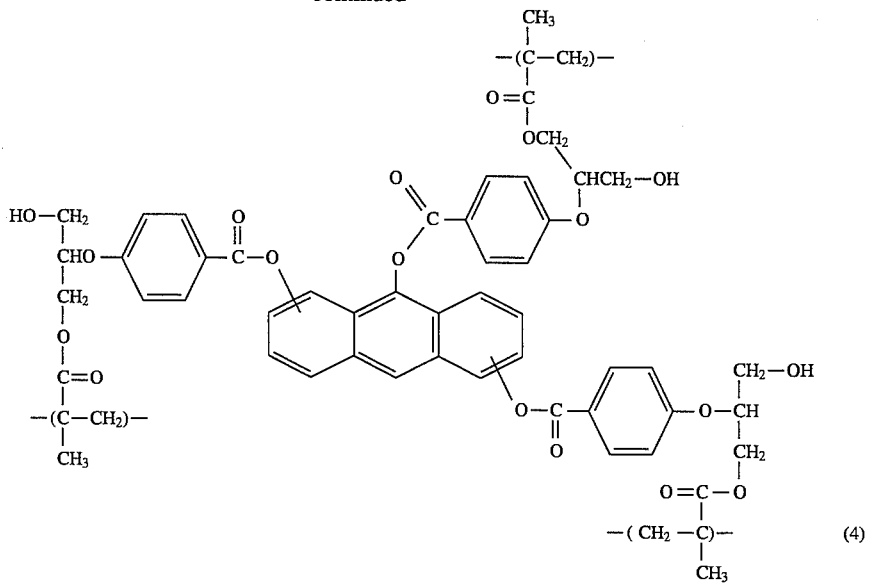

-continued

Next, a pattern is formed as follows. On the antireflection coating, a resist material for KrF excimer laser beams, for example, is spin coated, and baked to form a resist material. When exposed to deep ultraviolet light such as KrF excimer laser beams, the deep ultraviolet light such as KrF excimer laser beams transmitting via the resist film is absorbed due to the presence of anthracene ring in the antireflection coating to prevent the reflection from the semiconductor substrate. As a result, the undesirable influences caused by the in-layer multiple reflection which is a serious problem in this art can be prevented completely, resulting in causing no dimensional change even if a resist pattern is formed on a highly reflective substrate such as an aluminum wiring substrate, or a level different substrate.

Further, since the antireflection coating formed from the anthracene derivative of the formula [I] and a resin having one or more glycidyl groups is not dissolved in a solution of resist, there brings about no intermixture with the resist at the interface. Thus, the dimensional change of the resist pattern does not take place.

Compounds similar to the anthracene derivative of the formula [I] used as the crosslinking agent are disclosed in DE-OS 2,257,442 wherein three groups represented by the formula [II] are introduced into the 1, 8 and 9 positions of the anthracene ring at the same time, for example, 1,8,9-tris(4-hydroxybenzoyloxy)anthracene, 1,8,9-tris-(2-hydroxybenzoyloxy)anthracene, etc. But when these compounds are mixed with a resin having two or more glycidyl groups in the molecule and heated, the crosslinking reaction hardly proceeds due to stearic hindrance and/or strong intramolecular hydrogen bond, resulting in maintaining the solubility in acetone and a solvent for resist solutions. Therefore, when such compounds are used for making the antireflective coating, the desired antireflective coating cannot be obtained at all due to intermixture with the resist at the interface portion.

The anthracene compound of the formula [I] can also be used as an intermediate for medicines, dyes, etc., and a functional material for optical recording media, etc.

The present invention is explained in detail referring to Examples, in which all percents are by weight unless otherwise specified.

EXAMPLE 1

Synthesis of 2,6,9-tris(4-hydroxybenzoyloxy)anthracene (1) A suspension of p-hydroxybenzoic acid (200 g, 1.2 mole), benzyl chloride (190 g, 1.5 mole) and potassium carbonate (165 g, 1.2 mole) in acetone (1200 ml) was reacted with stirring for 12 hours under reflux. After cooling, the precipitate was filtered off, and the filtrate was concentrated until 400 ml. $H_2O$ (1 l) was added with stirring to the residue and the mixture was allowed to stand. The organic layer was separated, and concentrated, and the residue was added to a solution of NaOH (60 g, 1.5 mole) in $H_2O$ (1 l) and ethanol (500 ml), followed by stirring for 4 hours to be dissolved. Then conc. hydrochloric acid (200 ml) was added to make pH 1. The precipitate was filtered, washed with $H_2O$ and with ethanol, and dried to give 195 g of 4-benzyloxybenzoic acid as white crystals having a m.p. of 191.2°–192.6° C.

$^1$HNMR δ ppm (CDCl$_3$/DMSO-d$_6$): 5.10 (2H, s, ARCH$_2$O-), 6.92 (2H, d, J=8Hz, Ar 3-H, 5-H), 7.13–7.51

(5H, m, ArH), 7.86 (2H, d, J=8Hz, Ar 2-H,

6-H), 8.65 (1H, bs, OH).

IR (KBr-disk) ν cm$^1$: 1675 (COOH).

(2) To a suspension of 4-benzyloxybenzoic acid (16 g, 70 mmole) obtained in above (1) in methylene chloride (50 ml), thionyl chloride (20.6 g, 173 mmole) and N,N-dimethylformamide (2 drops) were added, and reacted with stirring at 45°–50° C. for 1 hour. After standing at room temperature overnight, the solvent was removed to give 17.3 g of 4-benzyloxybenzoyl chloride as white crystals.

(3) To a solution of 2,6-dihydroxy-9-anthrone (5 g, 22 mmole) in pyridine (110 ml) and triethylamine (8.8 g), 4-benzyloxybenzoyl chloride (17.0 g, 69 mmole) obtained in above (2) was added in a small portion. The mixture was reacted with stirring at 100° C. for 5 hours and cooled to room temperature. The reaction mixture was poured into 1N hydrochloric acid (600 ml), extracted with methylene chloride (250 ml). The methylene chloride layer was washed with 1N hydrochloric acid (600 ml×1) and then saturated aqueous NaCl solution (500 ml×3), and dried over anhydrous MgSO$_4$. After removing the drying agent and the solvent, the residual oil (26 g) was crystallized from a mixture of n-hexane and tetrahydrofuran [½ (v/v)] to afford 7.45 g of 2,6,9-tris(4-benzyloxybenzoyloxy)anthracene as yellow crystals having a melting point of 219°–221° C.

$^1$HNMR δ ppm (CDCl$_3$): 5.15, 5.17 and 5.20

(each 2H, each s, each ArC$\underline{H}_2$O-), 7.03–8.40

(34H, m, ArH).

IR (KBr-disk) ν cm$^{-1}$: 1728 (COO-).

(4) A solution of 2,6,9-tris(4-benzyloxybenzoyloxy)anthracene (6.2 g, 7.3 mmole) obtained in above (3) in tetrahydrofuran (250 m ml) was hydrogenated for 6 hours at room temperature at 1 atm. in the presence of 5% palladium on carbon (11.5 g). After reaction, catalyst was filtered off. The filtrate was concentrated and residual yellow solid (4.2 g) was re crystallized from a mixture of n-hexane and tetrahydrofuran [⅓ (v/v)] to give 3.0 g of 2,6,9-tris(4-hydroxybenzoyloxy)anthracene as pale yellow crystals having a melting point of 238° C. (decomp.).

$^1$HNMR δ ppm (DMSO-d$_6$): 6.90–7.04 (6H, m, (Ar 3'-H, 5'-H)×3), 7.50–8.29 (12H, m, (Ar 2'-H, 6'-H)×3) and Anthracene ring 1-H, 3-H, 4-H, 5-H, 7-H, 8-H), 8.67 (1H, s, Anthracene ring 10-H), 10.60 (3H, bs, O$\underline{H}$×3).

IR (KBr-disk) ν cm$^{-1}$: 3392 (OH), 1699 (COO-).

EXAMPLE 2

Synthesis of 2,6-bis(4-hydroxybenzoyloxy)anthracene (1) To a suspension of 2,6-dihydroxyanthraquinone (3 g, 12.5 mmole) and anhydrous potassium carbonate (23 g) in acetone (400 ml), dimethyl sulfate (20 g, 158 mmole) was added at room temperature. The resulting mixture was reacted with stirring for 6 hours under reflux. After standing at room temperature overnight, the reaction mixture was poured into cold H$_2$O (580 ml). The precipitate was filtered and dried. The resultant crude dark brown solid (3.1 g) was recrystallized from benzene to give 2.7 g of 2,6-dimethoxyanthraquinone as yellow-brown crystals.

$^1$HNMR δ ppm (DMSO-d$_6$): 3.97 (6H, s, C$\underline{H}_3$O×2), 7.43 (2H, d, J=8Hz, Anthraquinone ring 3-H, 7-H), 7.61 (2H, s, Anthraquinone ring 1-H, 5-H), 8.17 (2H, d, J=8Hz, Anthraquinone ring

4-H, 8-H).

IR (KBr-disk) ν cm$^{-1}$: 1668 (C=O)

(2) To a suspension of 2,6-dimethoxyanthraquinone (2.7 g, 10 mmole) obtained in above (1) in 25% aqueous ammonia (92 ml), zinc powder (10.2 g, 156 mmole) and cupric sulfate 5 hydrate (130 mg) were added. The resulting mixture was stirred for 7 hours at 70° C. and cooled to room temperature. The reaction mixture was neutralized with 1N sulfuric acid (40 ml). Methylene chloride and H$_2$O were added thereto with stirring. A precipitate was filtered off and the filtrate was separated. The organic layer separated was washed with H$_2$O, and evaporated. Residual crude solid (2.2 g) was recrystallized from methanol to give 1.3 g of 2,6-dimethoxyanthracene as yellow-brown crystals.

$^1$HNMR δ ppm (CDCl$_3$): 3.80 (6H, s, C$\underline{H}_3$O×2), 6.51–8.20 (8H, m, ArH).

IR (KBR-disk) ν cm$^{-1}$: 1613, 1577.

(3) To a suspension of 2,6-dimethoxyanthracene (1.22 g, 5.1 mmole) obtained in above (2) in methylene chloride (30 ml), a solution of boron tribromide (3.2 g, 12.8 mmole) in methylene chloride (10 ml) was added dropwise at −60° C. The temperature of the resulting mixture was raised slowly to room temperature, and allowed to stand at room temperature overnight. The reaction mixture was poured into cold H$_2$O (200 ml). The precipitate was filtered, washed with H$_2$O and dried to afford 0.85 g of 2,6-dihydroxyanthracene as a crude yellow-brown solid.

$^1$HNMR δ ppm (DMSO-d$_6$): 6.07–8.15 (8H, m, ArH), 9.65 (2H, bs, O$\underline{H}$×2).

(4) To a solution of 2,6-dihydroxyanthracene (0.82 g, 3.9 mmole) obtained in above (3) in pyridine (15 ml), 4-benzyloxybenzoyl chloride (2.12 g, 8.58 mmole) obtained in Synthesis Example 1, (1) was added, and then triethylamine (1 g) was added dropwise at 20° C. The resulting mixture was reacted with stirring for 8 hours at 90°–95° C. The reaction mixture was cooled, poured into dilute HCl (400 ml), extracted with methylene chloride. The organic layer separated was washed with H$_2$O and evaporated. The crude oily residue was chromatographed on silica gel (Wakogel C-200, a trade name, mfd. by Wako Pure Chemical Industries, Ltd.) with n-hexane/methylene chloride (7/1→2/1→ 1/143 1/2) as eluent to give 0.56 g of 2,6-bis(4-benzyloxybenzoyloxy)anthracene as a yellow powder.

$^1$HNMR δ ppm (CDCl$_3$): 5.09 and 5.17 (each 2H, each s, each ArC$\underline{H}_2$O-), 6.82–8.66 (26H, m, ArH).

IR (KBr-disk) ν cm$^{-1}$: 1732 (COO-).

(5) Using 2,6-bis(4-benzyloxybenzoyloxy)anthracene (0.56 g, 0.88 mmole) obtain in above (4), the catalytic reduction was carried out in the same manner as described in Example 1, (4) to afford 0.36 g of 2,6-bis(4-hydroxybenzoyloxy)anthracene as pale yellow crystals having a melting point of 324° C. (Decomp).

$^1$HNMR δ ppm (DMSO-d$_6$): 6.63–8.97 (16H, m, ArH), 10.48 (2H, bs, O$\underline{H}$×2).

IR (KBr-disk) ν cm$^{-1}$: 3405 (OH), 1701 (COO-).

EXAMPLE 3

Synthesis of 1,5,9-tris(4-hydroxybenzoyloxy)anthracene (1) To a suspension of 1,5-dihydroxyanthraquinone (10 g, 41.6 mmole) and stannous chloride (45 g, 237 mmole) in glacial acetic acid (150 ml), conc. hydrochloric acid (90 ml) was added at 16°–20° C. The resulting mixture was stirred for 4 hours under reflux. After standing at room temperature overnight, the reaction mixture was cooled to 5° C. A precipitate was filtered, washed with H2O and dried to afford 8.0 g of 1,5-dihydroxyanthrone as dark brown needles having a m.p. of 231°–233° C.

$^1$HNMR δ ppm (DMSO-d$_6$): 4.20 (2H, s, C$\underline{H}_2$), 6.87

(1H, d, J=8Hz, Anthracene ring 6-H), 7.09 (1H, d, J=8Hz, Anthracene ring 2-H), 7.19 (1H, d, J=8Hz, Anthracene ring 4-H), 7.35 (1H, t, J=8Hz, Anthracene ring 7-H), 7.57 (1H, t, J=8Hz, Anthracene ring 3-H), 7.69 (1H, d, J=8Hz, Anthracene ring 8-H), 10.23 (1H, bs, 5-O$\underline{H}$), 12.97 (1H, s, 1-O$\underline{H}$).

IR (KBr-disk) ν cm$^{-1}$: 3338 (OH), 1633 (C=O).

(2) To a solution of 1,5-dihydroxyanthrone (2.3 g, 10 mmole) obtained in above (1) in pyridine (45 ml) and triethylamine (3.6 g), 4-benzyloxybenzoyl chloride (8 g) obtained in Synthesis Example 1, (2) was added in a small portion, continued to stir for 5 hours at 90° C., and allowed to stand at room temperature overnight. The reaction mixture was poured into 1N hydrochloric acid (300 ml), extracted with methylene chloride. The organic layer separated was washed with $H_2O$, dried over anhydrous $MgSO_4$ and evaporated. The residue was chromatographed on silica gel (Wakogel C-200, a trade name, mfd. by Wako Pure Chemical Industries, Ltd.) with n-hexane/methylene chloride (1/1→1/3) as eluent to afford 2.0 g of 1,5,9-tris(4-benzyloxybenzoyloxy)anthracene as yellow crystals having a m.p. of 240°–242° C.

$^1$HNMR δ ppm ($CDCl_3$): 5.00, 5.03 and 5.23
(each 2H, each s, each $ArCH_2O$-), 6.67–8.54
(34H, m, ArH).

IR (KBr-disk) ν $cm^{-1}$: 1735 (COO-).

(3) Using 1,5,9-tris(4-benzyloxybenzoyloxy)anthracene (1 g, 1.14 mmole) obtained in above (2), the catalytic reduction was carried out in the same manner as described in Example 1, (4). The resulting crude solid (0.7 g) was recrystallized from a mixture of tetrahydrofuran and n-hexane to give 0.5 g of 1,5,9-tris(4-hydroxybenzoyloxy)anthracene as pale yellow crystals having a m.p. of 326°.

$^1$HNMR δ ppm (DMSO-$d_6$): 6.55–7.06 (6H, m, Phenyl ring (3-H, 5-H)×3), 7.32–8.23 (12H, m,
Anthracene ring 2-H, 3-H, 4-H, 6-H, 7-H, 8-H
and Phenyl ring (2-H, 6-H)×3), 8.65 (1H, s,
Anthracene ring 10-H), 10.41 (3H, bs, O$\underline{H}$×3).

IR (KBr-disk) ν $cm^{-1}$: 3408 (OH), 1702 (COO-).

EXAMPLE 4

Synthesis of 1,2,10-tris(4-hydroxybenzoyloxy)anthracene (1) Using 1,2-dihydroxy-10-anthrone (2.26 g) and 4-benzyloxybenzoyl chloride (8 g) obtained in Example 1, (2), the reaction was carried out in the same manner as described in Example 1, (3). The resulting crude solid (3.5 g) was chromatographed on silica gel (Wakogel C-200, a trade name, mfd. by Wako Pure Chemical Industries, Ltd.) with n-hexane/methylene chloride [4/1→2/1→1/1(v/v)] as eluent to give 1.6 g of 1,2,10-tris(4-benzyloxybenzoyloxy)anthracene as yellow crystals.

$^1$HNMR δ ppm ($CDCl_3$): 5.09, 5.16 and 5.23 (each 2H, each s, each AR$CH_2$O-), 6.91–8.44 (34H, m, ArH).

IR (KBr-disk) ν $cm^{-1}$: 1740 (COO-).

(2) Using 1,2,10-tris(4-benzyloxybenzoyloxy)anthracene (1.54 g, 1.8 mmole) obtained in above (1), the catalytic reduction was carried out in the same manner as described in Example 1, (4). The resulting crude solid (0.92 g) was recrystallized from a mixture of tetrahydrofuran and n-hexane to give 0.5 g of 1,2,10-tris(4-hydroxybenzoyloxy)anthracene as pale yellow crystals.

$^1$HNMR δ ppm (DMSO-$d_6$): 6.79–7.08 (6H, m, Phenyl ring (3-H, 5-H)×3), 7.49–8.29 (12H, m,
Anthracene ring 3-H, 4-H, 5-H, 6-H, 7-H, 8-H
and Phenyl ring (2-H, 6-H)×3), 8.59 (1H, s,
Anthracene ring 9-H), 10.59 (3H, bs, O$\underline{H}$×3).

IR (KBr-disk) ν $cm^{-1}$: 3413 (OH), 1706 (COO-).

EXAMPLE 5

Synthesis of 2,6,9-tris(4-hydroxy-3-methoxybenzoyloxy)anthracene (1) To a suspension of 4-hydroxy-3-methoxybenzoic acid (25 g, 0.15 mole) in ethanol (150 ml), 2N NaOH aq. (74.3 g, 0.15 mole) and benzyl chloride (56.5 g, 0.45 mole) were added, continued to stir for 1 hour under reflux, then 5N NaOH aq. (150 ml) was added dropwise with stirring under reflux, and continued to stir for 1 hour under reflux. After reaction, the solvent was removed, and $H_2O$ was added to the residue and acidified with conc. hydrochloric acid to make pH 1. The resulting precipitate was filtered, washed with $H_2O$ and dried to give 22.1 g of 4-benzyloxy-3-methoxybenzoic acid as pale yellow crystals having a m.p. of 171°–172.5°.

$^1$HNMR δ ppm (DMSO-$d_6$): 3.81 (3H, s, $CH_3$O-), 5.16 (2H, s, AR$CH_2$O-), 7.13 (1H, d, J=8Hz, Ar 5-H), 7.33–7.44 (5H, m, ArH), 7.47 (1H, d, J=2Hz, Ar 2-H), 7.54 (1H, dd, J=2Hz and 8Hz, Ar 6-H).

IR (KBr-disk) ν $cm^{-1}$: 1676 (COOH).

(2) A suspension of 4-benzyloxy-3-methoxybenzoic acid (22.3 g, 86.3 mmole) obtained in above (1) in thionyl chloride (30.8 g, 0.26 mole) was heated slowly, and reacted with stirring for 2 hours at 60°–65° C. The reaction mixture was concentrated to afford 23.4 g of 4-benzyloxy-3-methoxybenzoyl chloride as pale yellow leaflets having a m.p. of 63°–65° C.

(3) Using 4-benzyloxy-3-methoxybenzoyl chloride (10.1 g, 36.4 mmole) obtained in above (2) and 2,6-dihydroxy-9-anthrone (2.2 g, 11 mmole), the reaction was carried out in the same manner as described in Example 1, (3) to afford 7.8 g of 2,6,9-tris(4-benzyloxy-3-methoxybenzoyloxy)anthracene as pale yellow crystals having a m.p. of 186°–189° C.

$^1$HNMR δ ppm ($CDCl_3$): 3.96, 3.99 and 4.00 (each 3H, each s, each $CH_3$O-), 5.25, 5.27 and 5.29
(each 2H, each s, each AR$CH_2$O-), 6.93–8.09
(30H, m, ArH), 8.39 (1H, Anthracene ring
10-H).

IB (KBr-disk) ν $cm^{-1}$: 1736 (COO-).

(4) Using 2,6,9-tris(4-benzyloxy-3-methoxybenzoyloxy) anthracene (2.4 g, 2.52 mmole) obtained in above (3), the catalytic reduction was carried out in the same manner as described in Example 1, (4). The resulting crude solid (1.6 g) was recrystallized from a mixture of tetrahydrofuran and n-hexane to give 0.9 g of 2,6,9-tris(4-hydroxy-3-methoxybenzoyloxy)anthracene as pale yellow crystals having a m.p. of 206° C. (Decomp.).

$^1$HNMR δ pm (DMSO-$d_6$): 3.94, 3.97 and 3.98
(each 3H, each s, each $CH_3$O-), 7.01–8.39
(15H, m, ArH), 8.78 (1H, s, Anthracene ring
10-H), 10.33 (3H, bs, O$\underline{H}$×3).

IR (KBr-disk) ν $cm^{-1}$: 3374 (OH), 1728 (COO-).

EXAMPLE 6

Synthesis of 2,6,9-tris(3,4-dihydroxybenzoyloxy)anthracene (1) To a suspension of 3,4-dihydroxybenzoic acid (25.4 g, 0.17 mle) in ethanol (250 ml), 5N NaOH aq. (270 ml) and benzyl chloride (102 g, 0.81 mole) were added. The resulting mixture was reacted with stirring for 6 hours under reflux. The reaction mixture was cooled to room temperature, allowed to stand at same temperature overnight and acidified with conc. hydrochloric acid (40 ml). The precipitate was filtered, washed with hot ethanol and dried under reduced pressure to give 38.2 g of 3,4-dibenzyloxybenzoic acid as pale yellow crystals having a m.p. of 184°–186° C.

¹HNMR δ ppm (DMSO-d₆): 3.38 (1H, bs, O<u>H</u>), 5.18 and 5.22 (each 2H, each s, each ArC<u>H</u>₂O-), 7.16

(1H, d, J=8.8Hz, Ar 5-H), 7.30 - 7.57 (12H, m, ArH).

IR (KBr-disk) ν cm⁻¹: 1679 (C=O).

(2) A mixture of 3,4-dibenzyloxybenzoic acid (10 g, 30 mmole) obtained in above (1) and thionyl chloride (10.7 g, 90 mmole) was heated slowly, reacted with stirring for 1 hour at 85° C. and then evaporated in vacuo to give 10.3 g of 3,4-dibenzyloxy benzoyl chloride as white crystals having a melting point of 92.5°–94.5° C.

(3) Using 3,4-dibenzyloxyenzoyl chloride (5.2 g, 14.6 mmole) obtained in above (2) and 2,6-dihydroxy-9-anthrone (1 g, 4.4 mmole), the reaction was carried out in the same manner as described in Example 1, (3). The resulting crude solid (5.4 g) was recrystallized from methylene chloride/ ethyl acetate (¼) to afford 3.4 g of 2,6,9-tris(3,4-dibenzyloxybenzoyloxy)anthracene as yellow crystals having a m.p. 189°–191° C.

¹HNMR δ ppm (CDCl₃): 5.20–5.31 (12H, m,

ArC<u>H</u>₂O-×6), 7.14–8.05 (44H, m, ArH), 8.21 (1H, d, J=9.2Hz, Anthracene ring 4-H), 8.58 (1H, s, Anthracene ring 10-H).

IR (KBr-disk) ν cm⁻¹: 1733 (COO-).

(4) Using 2,6,9-tris(3,4-dibenzyloxybenzoyloxy)anthracene (2 g, 1.7 mmole) obtained in above (3), the catalytic reduction was carried out in the same manner as described in Example 1, (4). The resulting crude solid (1.8 g) was recrystallized from tetrahydrofuran/n-hexane (5/1) to afford 1.2 g of 2,6,9-tris(3,4dihydroxybenzoyloxy)anthracene as pale yellow crystals having a m.p. of 233° C. (Decomp.).

¹HNMR δ ppm (DMSO-d₆): 6.87–8.08 (14H, m, ArH), 8.27 (1H, d, J=9.2Hz, Anthracene ring 4-H), 8.67 (1H, s, Anthracene ring 10-H), 9.77 (6H, bs, O<u>H</u>×6).

IR (KBr-disk) ν cm⁻¹: 3365 (OH), 1701 (COO-).

EXAMPLE 7

Synthesis of 1,2,10-tris(3-chloro-4-hydroxybenzoyloxy) anthracene (1) Using 3-chloro-4-hydroxybenzoic acid·½ hydrate (25 g, 0.14 mole) and benzyl chloride (52.3 g, 0.41 mole), the reaction was carried out in the same manner as described in Example 1, (1) to give 20.4 g of 4-benzyloxy-3-chlorobenzoic acid as white crystals having a m.p. 211°–213° C.

¹HNMR δ ppm (DMSO-d₆): 5.30 (2H, s, ArC<u>H</u>₂O-), 7.34 (1H, d, J=8.4Hz, Ar 5-H), 7.37–7.49 (5H, m, ArH), 7.88 (1H, dd, J=1.8Hz and 8.4Hz, Ar 6-H), 7.93 (1H, d, J=1.8Hz, Ar 2-H), 11.15 (1H, bs, COO<u>H</u>).

IR (KBr-disk) ν cm⁻¹: 1683 (COOH).

(2) Using 4-benzyloxy-3-chlorobenzoic acid (2.0 g, 7.6 mmole) obtained in above (1), the reaction was carried out in the same manner as described in Example 1, (2) to give 2.1 g of 4-benzyloxy-3-chlorobenzoylchloride as light brown crystals having a m.p. of 78°–80° C.

IR (KBr-disk) ν cm⁻¹: 1751 (C=O).

(3) Using 4-benzyloxy-3-chlorobenzoyl chloride (1.6 g, 5.7 mmole) obtained in above (2) and 1,2-dihydroxy-10-anthrone (0.4 g, 1.7 mmole), the reaction was carried out in the same manner as described in Example 1, (3). The resulting crude solid (1.1 g) was chromatographed on silica gel (Wakogel C-200, a trade name, mfd. by Wako Pure Chemical Industries, Ltd.) with n-hexane/methylene chloride [4/1→3/1→1/1(v/v)] as eluent to give 0.65 g of 1,2,10-tris(4-benzyloxy-3-chlorobenzoyloxy)anthracene as pale yellow crystals having a m.p. of 106°–109 ° C.

¹HNMR δ ppm (CDCl₃): 5.18, 5.25 and 5.33 (each 2H, each s, each ArC<u>H</u>₂O-), 6.91–8.46 (30H, m, ArH), 8.49 (1H, s, Anthracene ring 9-H).

IR (KBr-disk) ν cm⁻¹: 1743 (COO-).

(4) Using 1,2,10-tris(4-benzyloxy-3-chlorobenzoyloxy) anthracene (280 mg, 0.4 mmole) obtained in above (3), the catalytic reduction was carried out in the same manner as described in Example 1, (4) to afford 0.2 g of 1,2,10-tris(3-chloro-4-hyroxybenzoyloxy)anthracene as white crystals having a m.p. of 238° C.

¹HNMR δ ppm (Acetone-d₆): 6.98–8.41 (15H, m ArH), 8.52 (1H, s, Anthracene ring 9-H), 10.41

(3H, bs, O<u>H</u>×3).

IR (KBr-disk) ν cm⁻¹: 3382 (OH), 1747 (COO-).

SYNTHESIS EXAMPLE 8

Synthesis of 1,2,10-tris(3-hydroxy-4-methylbenzoyloxy) anthracene (1) Using 3-hydroxy-4-methylbenzoic acid (20.3 g, 0.13 mole)and benzyl chloride (50.8 g, 0.40 mole), the reaction was carried out in the same manner as described in Example 1, (1). The resulting crude solid was recrystallized from ethanol to give 15.0 g of 3-benzyloxy-4-methylbenzoic acid as white crystals having a m.p. of 159°–161° C.

¹HNMR δ ppm (DMSO-d₆): 2.26 (3H, s, C<u>H</u>₃), 5.18 (2H, s, ARC<u>H</u>₂O-), 7.27–7.43 (6H, m, ArH and Phenyl ring 5 -H), 7.47 (1H, s, Phenyl ring 2-<u>H</u>), 7.51 (1H, d, J=7.7Hz, Phenyl ring 6-H), 12.81 (1H, bs, COO<u>H</u>).

IR (KBr-disk) ν cm⁻¹: 1690 (COOH).

(2) Using 3-benzyloxy-4-methylbenzoic acid (3.0 g, 12.4 mmole) obtained in above (1), the reaction was carried out in the same manner as described in Example 1, (2) to give 3.12 g of 3-benzyloxy-4-methylbenzoyl chloride as pale yellow crystals having a melting point of 49°–51° C.

IR (KBr-disk) ν cm⁻¹: 1741 (C=O).

(3) Using 3-benzyloxy-4-methylbenzoyl chloride (2.85 g, 10.9 mmole) obtained in above (2) and 1,2-dihydroxy-10-anthrone (0.75 g, 3.3 mmole), the reaction was carried out in the same manner as described in Example 1, (3). The resulting residue was chromatographed on silica gel (Wakogel C-200) with methylene chloride as eluent to give 160 mg of 1,2,10-tris(3-benzyloxy-4-methylbenzoyloxy)anthracene as yellow crystals having a melting point of 132°–135° C.

¹HNMR δ ppm (CDCl₃): 2.17, 2.27 and 2.31

(each 3H, each s, each C<u>H</u>₃), 5.03, 5.15 and 5.24 (each 2H, each s, each ArC<u>H</u>₂O-), 7.15–8.07 (30H, m, ArH), 8.45 (1H, s, Anthracene ring 9-H).

IR (KBr-disk) ν cm⁻¹: 1737 (COO-).

(4) Using 1,2,10-tris(3-benzyloxy-4-methylbenzoyloxy) anthracene (150 mg, 0.17 mmole) obtained in above (3), the catalytic reduction was carried out in the same manner as described in Example 1, (4) to give 80 mg of 1,2,10-tris(3- hydroxy-4-methylbenzoyloxy)anthracene as white crystals having a m.p. 251° C. (Decomp.).

$^1$HNMR δ ppm (Acetone-d$_6$): 2.22, 2.25 and 2.27 (each 3H, each s, each CH$_3$), 6.95–8.26 (15H, m, ArH), 8.56 (1H, s, Anthracene ring 9-H), 10.11 (3H, bs, OH×3).

IR (KBr-disk) ν cm$^{-1}$: 3409 (OH), 1716 (COO-).

REFERENCE EXAMPLE 1

Synthesis of poly(methyl methacrylate/glycidyl methacrylate/2,3-dihydroxypropyl methacrylate)

(1) To a solution of methyl methacrylate (50.1 g, 0.5 mole) and glycidyl methacrylate (28.4 g, 0.2 mole) in toluene (240 ml), 2,2-azobis(methyl 2-methylpropionate) (0.8 g) was added. Then the mixture was reacted with stirring at 80° C. for 7 hours under nitrogen. After cooling, the reaction mixture was poured into methanol (200 ml) and the polymer was precipitated. The polymer was filtered and dried under reduced pressure to give 77 g of poly(methyl methacrylate/glycidyl methacrylate) as a white powder having $\overline{Mw}$ 35800 and $\overline{Mn}$ 19200 (GPC with polystyrene calibration). The composition of the polymer was found to be methyl methacrylate unit and glycidyl methacrylate unit in molar ratio of ca. 5:2 based on $^1$HNMR analysis.

(2) To a solution of poly(methyl methacrylate/glycidyl methacrylate) (5 g) obtained in above (1) in tetrahydrofuran (50 ml), 1N sulfuric acid 10 ml) was added. The resulting mixture was reacted with stirring at 40° C. for 1 hour, cooled to 10° C. and poured into H$_2$O (500 ml). The precipitate was filtered, washed with H$_2$O and dried under reduced pressure to afford 2.5 g of poly(methyl methacrylate/glycidyl methacrylate/2,3-dihydroxyproyl methacrylate) as a white powder having $\overline{Mw}$ 36300 and $\overline{Mn}$ 20200 (GPC with polystyrene calibration). The composition of the polymer was found to be methyl methacrylate unit and glycidyl methacrylate unit and 2,3-dihydroxypropyl methacrylate unit in molar ratio of ca. 5:1:1 based on $^1$HNMR analysis.

REFERENCE EXAMPLE 2

An antireflection coating material having the following composition was prepared:

| | |
|---|---|
| poly(methyl methacrylate/glycidyl methacrylate/2,3-dihydroxypropyl methacrylate) (the resin of Reference Example 1) | 4.0 g |
| 2,6,9-tris(4-hydroxybenzoyloxy)anthracene (the compound of Example 1) | 1.0 g |
| tetrahydrofurfuryl alcohol | 45.0 g |
| propylene glycol monomethyl ether acetate | 50.0 g |

The above-mentioned composition was spin coated on a substrate (silicon wafer) and baked at 200° C. for 20 seconds on a hot plate to give a deep ultraviolet absorbing material film with 100 nm thick. Then, the resulting film was subjected to measurement with ultraviolet (UV) light.

FIG. 1 shows UV spectrum. As is clear from FIG. 1, the film has an absorption at near 250 nm.

The deep ultraviolet absorbent film was not dissolved in acetone at all. This showed that crosslinking reaction took place.

REFERENCE EXAMPLE 3

A chemically amplified positive resist material having the following composition was prepared:

| | |
|---|---|
| poly[p-(ethoxyethoxy)styrene/hydroxystyrene] | 2.50 g |
| 2-cyclohexylcarbonyl-2-(p-toluenesulfonyl)propane | 0.13 g |
| propylene glycol monomethyl ether acetate | 7.37 g |

The pattern formation on a highly reflective substrate having a level difference using the composition of Reference Example 2 as the antireflection coating material and the above-mentioned resist material as the chemically amplified positive resist material is explained referring to FIG. 2A to 2E.

Figure 2B:
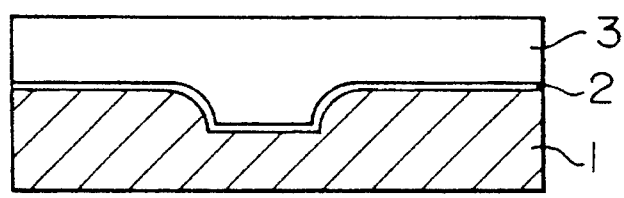
Figure 2C:
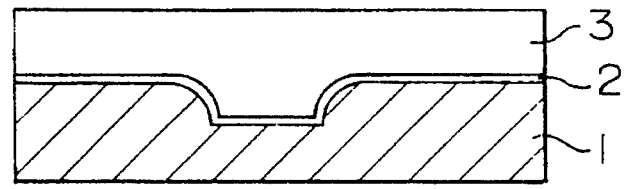
Figure 2D:
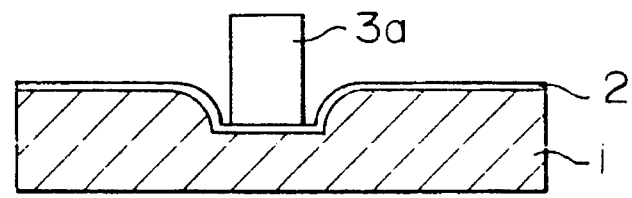
Figure 2E:
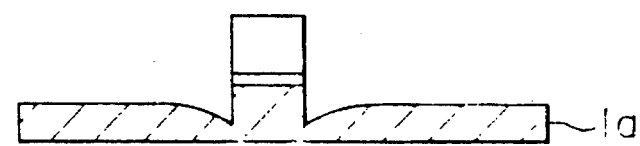

On an aluminum level difference substrate 1 having high reflectivity obtained by subjecting a silicon subject to photolithography, etching, and aluminum sputtering, the antireflection coating material 2 of Reference Example 2 was spin coated and baked at 200° C. for 90 seconds on a hot plate to give an antireflection coating of 100 nm thick (FIG. 2A) and insoluble in acetone at all. Then, the chemically amplified positive resist material 3 mentioned above was spin coated on the antireflection coating, and prebaked at 90° C. for 90 second on a hot plate to give a resist material film of 1.0 μm thick (FIG. 2B). Then, the resulting substrate was exposed selectively via a mask 5 to KrF excimer laser beams 4 (248.4 nm) (FIG. 2C). After post baking at 100° C. for 90 seconds on a hot plate, development with an alkaline developing solution (an aqueous solution of 2.38% tetramethylammonium hydroxide) was carried out for 60 seconds to remove only exposed portions of the resist material 3 by dissolution. As a result, the positive type pattern 3a was obtained (FIG. 2D). The obtained positive type pattern had a resolution of line and space of 0.25 μm with good pattern shape (a rectangle). The exposing light amount was about 30 mJ/cm$^2$. Then, using the pattern 3a as a mask, the deep ultraviolet light absorbing material film 2 and the aluminum substrate 1 were etched with an oxygen gas and a chlorine-based gas in this order (FIG. 2E). The formed etching pattern 1a had the same size as the resist pattern 3a without causing dimensional change with a good pattern.

REFERENCE EXAMPLES 4 TO 10

Antireflection coating materials having compositions as shown in Table 1 were prepared.

TABLE 1

| Reference Example No. | Composition | Amount (g) |
|---|---|---|
| 4 | Poly(methyl methacrylate/glycidyl methacrylate/2,3-dihydroxypropyl methacrylate) | 4.0 |
| | 1,5,9-Tris(4-hydroxybenzoyloxy)anthracene (Compound of Example 3) | 1.0 |
| | Tetrahydrofurfuryl alcohol | 45.0 |
| | Propylene glycol monomethyl ether acetate | 50.0 |
| 5 | Poly(methyl methacrylate/glycidyl methacrylate/2,3-dihydroxypropyl methacrylate) | 4.0 |
| | 2,6-Bis(4-hydroxybenzoyloxy)anthracene (Compound of Example 2) | 2.0 |
| | Diethylene glycol dimethyl ether | 94.0 |
| 6 | Poly(methyl methacrylate/glycidyl methacrylate/2,3-dihydroxypropyl methacrylate) | 4.0 |
| | 2,6,9-Tris(3,4-dihydroxybenzoyloxy)anthracene (Compound of Example 6) | 2.0 |
| | Ethyl lactate | 19.0 |
| | Propylene glycol monomethyl ether | 75.0 |

TABLE 1-continued

| Reference Example No. | Composition | Amount (g) |
|---|---|---|
| | acetate | |
| 7 | Poly(methyl methacrylate/glycidyl methacrylate/2,3-dihydroxypropyl methacrylate) | 5.5 |
| | 1,2,10-Tris(4-hydroxybenzoyloxy)-anthracene (Compound of Example 4) | 1.5 |
| | Propylene glycol monomethyl ether acetate | 93.0 |
| 8 | Poly(methyl methacrylate/glycidyl methacrylate/2,3-dihydroxypropyl methacrylate) | 4.0 |
| | 1,2,10-Tris(3-hydroxy-4-methylbenzoyloxy)anthracene (Compound of Example 8) | 2.0 |
| | Ethyl lactate | 24.0 |
| | Propylene glycol monomethyl ether acetate | 70.0 |
| 9 | Poly(methyl methacrylate/glycidyl methacrylate/2,3-dihydroxypropyl methacrylate) | 4.0 |
| | 1,2,10-Tris(3-chloro-4-hydroxybenzoyloxy)anthracene (Compound of Example 7) | 2.0 |
| | Methyl 3-methoxypropionate | 15.0 |
| | Propylene glycol monomethyl ether acetate | 79.0 |
| 10 | Poly(methyl methacrylate/glycidyl methacrylate/2,3-dihydroxypropyl methacrylate) | 4.0 |
| | 2,6,9-Tris(3,4-hydroxy-3-methoxybenzoyloxy)anthracene (Compound of Example 5) | 1.0 |
| | Tetrahydrofurfuryl alcohol | 45.0 |
| | Propylene glycol monomethyl ether acetate | 50.0 |

Using the above-mentioned antireflection coating materials, patterns were formed in the same manner as described in Reference Example 3 by forming an antireflection coating on a highly reflective aluminum level difference substrate, and using the same chemically amplified positive resist material as used in Reference Example 3.

The results are shown in Table 2.

TABLE 2

| Reference Example No. | Exposed light amount (mJ/cm$^2$) | 0.25 μm Pattern | Halation |
|---|---|---|---|
| 4 | 30 | Good shape | Effective for prevention |
| 5 | 32 | Good shape | Effective for prevention |
| 6 | 28 | Good shape | Effective for prevention |
| 7 | 30 | Good shape | Effective for prevention |
| 8 | 30 | Good shape | Effective for prevention |
| 9 | 28 | Good shape | Effective for prevention |
| 10 | 31 | Good shape | Effective for prevention |

These deep ultraviolet absorbent films (Reference Examples 4 to 10) were not dissolved in acetone at all. These results showed that crosslinking reaction took place between the anthracene derivatives and the resin having one or more glycidyl groups.

REFERENCE EXAMPLE 11

A film forming material having the following composition was prepared:

| | |
|---|---|
| Poly(methyl methacrylate/glycidyl methacrylate/2,3-dihydroxypropyl methacrylate) [resin of Reference Example 1] | 4.0 g |
| 1,8,9-Tris(4-hydroxybenzoyloxy)anthracene [compound disclosed in DE-OS 2,257,442] | 1.0 g |
| Tetrahydrofurfuryl alcohol | 45.0 g |
| Propylene glycol monomethyl ether acetate | 50.0 g |

The above-mentioned composition was spin coated on a substrate (silicon wafer) and baked at 200° C. for 90 seconds by a hot plate to give an absorbent film of 100 μm thick. When the absorbent film was immersed in acetone, it was easily dissolved.

This means that when 1,8,9-tris(4-hydroxybenzoyloxy)anthracene is used, no crosslinking reaction proceeds, resulting in failing to obtain a deep ultraviolet absorbent film applying crosslinking reaction.

As mentioned above, when an anthracene derivative of the formula [I] is mixed with a resin having at least one glycidyl group and coated on a highly reflective substrate made of aluminum, aluminum-silicon, or polysilicon, etc. or a level difference substrate as an undercoating material for an exposing resist material for deep ultraviolet light (300 nm or less) and KrF excimer laser beams (248.4 nm), there can be obtained good pattern shape with a quarter micron order without generating notching or halation which often causes disconnection of the substrate, while maintaining high resolution ability and high sensitivity. Thus, the anthracene derivative of the formula [I] has a great value in forming ultra-fine patterns in semiconductor industry.

What is claimed is:

1. An anthracene derivative of the formula:

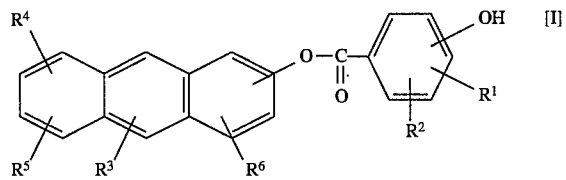

wherein $R^1$ and $R^2$ are independently a hydrogen atom, an alkyl group, an alkoxy group, a halogen atom or a hydroxyl group; $R^3$, $R^4$, $R^5$ and $R^6$ are independently a hydrogen atom, an alkyl group, an alkoxy group, a halogen atom, or a group of the formula:

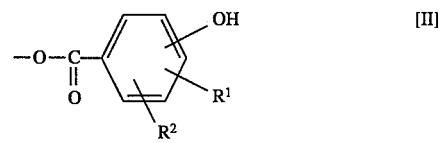

wherein $R^1$ and $R^2$ are as defined above, provided that at least one of $R^3$ through $R^6$ is the group of the formula [II], and the group of the formula [II] in number of 3 cannot be positioned at the 1, 8 and 9 positions of the anthracene ring at the same time.

2. An anthracene derivative according to claim 1, wherein one of $R^3$ through $R^6$ in the formula [I] is a group of the formula [II].

3. An anthracene derivative according to claim 1, wherein two of $R^3$ through $R^6$ in the formula [I] are a group of the formula [II].

4. An anthracene derivative according to claim 1, wherein one or more phenolic hydroxyl groups in the formulae [I] and [II] are positioned at para and/or meta positions with regard to the -OCO- group.

5. An anthracene derivative according to any one of claims 1–4 for use in a process for forming an antireflection coating when forming a pattern on a semiconductor substrate.

* * * * *